United States Patent [19]
Uemiya et al.

[11] Patent Number: 5,178,616
[45] Date of Patent: Jan. 12, 1993

[54] METHOD AND APPARATUS FOR INTRAVASCULAR LASER SURGERY

[75] Inventors: Takafumi Uemiya; Shin-ichiro Niwa; Koro Yotsuya; Ichiro Sogawa; Shin-ichi Kanazawa, all of Osaka, Japan

[73] Assignee: Sumitomo Electric Industries, Ltd., Osaka, Japan

[21] Appl. No.: 845,825

[22] PCT Filed: Jun. 6, 1989

[86] PCT No.: PCT/JP89/00574
§ 371 Date: Feb. 6, 1990
§ 102(e) Date: Feb. 6, 1990

[87] PCT Pub. No.: WO89/11833
PCT Pub. Date: Dec. 14, 1989

Related U.S. Application Data

[63] Continuation of Ser. No. 460,087, Feb. 6, 1990, abandoned.

[30] Foreign Application Priority Data

Jun. 6, 1988 [JP] Japan .................... 63-138766

[51] Int. Cl.⁵ .................................... A61B 17/36
[52] U.S. Cl. .................................... 606/7; 606/3; 606/10
[58] Field of Search ............ 606/2, 3, 7, 10, 11, 606/12, 17; 128/395-398; 219/121.6, 121.62

[56] References Cited

U.S. PATENT DOCUMENTS 3,935,472  1/1976  Bethea et al. .
4,408,602  10/1983 Nakajima .................... 606/10
4,418,688  12/1983 Loeb .
4,454,882  6/1984  Takano ...................... 128/395
4,784,132  11/1988 Fox et al. .................... 606/15
4,791,927  12/1988 Menger ....................... 606/3

FOREIGN PATENT DOCUMENTS 0217165  4/1987  European Pat. Off. .
51-35588  3/1976  Japan .
57-64049  4/1982  Japan .

OTHER PUBLICATIONS

U. Osterberg et al, "Dye Lase pumped byND: YAG laser pulses . . .", Optics Letters, Aug. 1986, 516-518.

Primary Examiner—Peter A. Aschenbrenner
Attorney, Agent, or Firm—Cushman, Darby & Cushman

[57] ABSTRACT

An intravascular laser operating device and method for examining and removing a diseased part in a blood vessel. The device includes a catheter having endoscopic fibers for performing an endoscopy and diagnostic of a diseased part in a blood vessel and laser light projecting fibers for projecting a laser light, a visible guide light, and an excited light to the diseased part. An laser device applies laser light to converting elements. A first wave length converting element converts part of the laser light into the visible guide light, and a second wave length converting element converts a part of the visible guide light into the excited light. The excited light is used for generating a fluorescent spectrum. An image is received representing the condition of the inside of the blood vessel based on image light received by the endoscopic fibers. A spectrum analyzing unit diagnoses the diseased part by obtaining the components of the fluorescent spectrum of the received image light. Then the diseased part is destroyed by the laser light which is positioned using the visible guide light.

5 Claims, 3 Drawing Sheets

METHOD AND APPARATUS FOR INTRAVASCULAR LASER SURGERY

This is a continuation of application Ser. No. 07/460,087, filed on Feb. 6, 1990, now abandoned.

FIELD OF THE INVENTION

The present invention relates to a laser operating device for intravascular surgery, and more in particular to a laser operating device for intravascular surgery which is used for examining and removing a diseased part in a blood vessel using laser light.

BACKGROUND OF THE INVENTION

In the prior art, there have been contrived various kinds of medical treatment diagnosis devices and methods thereof for removing such as a stenosis or occlusion of a blood vessel and an atheroma due to such as an arteriosclerosis.

A bypass operation is the most assured treatment method in which a lesion is completely removed by replacing a blood vessel including a diseased part with one of patient's own blood vessels or with an artificial blood vessel for example. However, since this method is followed by a surgery in which tissue is cut open, the vital body is subjected to a burden and a large amount of cost is needed for the treatment. Moreover, although a drug treatment is also adopted, it is effective only for solution of a thrombus and it has been difficult to remove an arteriosclerosis focus.

Therefore, there has been recently adopted a treatment that a catheter is inserted into a blood vessel from the outside of a body and the diseased part reached so as to directly remove a cause of an obstacle.

One is a treatment that a balloon catheter having a balloon attached on its distal tip portion is used and the balloon is expanded when the diseased part is reach so that the stenosis of the blood vessel is mechanically expanded. However, since the stenosis is simply expanded, e.g. the diseased focus of the arteriosclerosis or thrombus which causes a stenosis can not be removed and a probability of a relapse of a disease in a short period is high. Moreover, in cases where the blood vessel is entirely so occluded that the balloons can not be inserted and the arteriosclerosis is so advanced as to cause a calcification, it becomes difficult to treat by using a balloon.

The other is a method using laser light such as YAG laser or argon laser, wherein a metallic or ceramic chip attached to the tip of the catheter is heated by the laser light projected from the tip of an optical fiber so that the heated chip is pressed onto the diseased part so as to burn out the diseased part. According to this method, though the diseased part can be removed, the control of the light heating power is difficult and if the chip is overheated, a normal vessel wall is damaged or carbonized so that there may cause a new risk of vascular perforation or a new restenosis. Moreover, in case the vessel is tortuous or completely occluded, the chip method is not available because it can not be inserted.

Therefore, a method has been adopted in which the laser light from such as YAG laser, argon laser and excimer laser is directly projected onto the diseased part from the tip of the fiber so as to vaporize the diseased part. Since the portion having the laser light projected thereon is directly vaporized, the laser light is available also for a completely occluded diseased part and upon controlling the output of the laser light source and a pulse width and pulse interval of the pulse laser, a power control is possible with high accuracy.

In the intravascular laser operating device of a directly projecting type in the prior art as mentioned above, upon inserting the guide catheter up to the diseased part fibers and a tube necessary for diagnosis and treatment are alternately inserted.

For example, in the case of diagnosis and treatment of a diseased part in a vessel, first, endoscopic optical fibers and illumination optical fibers are inserted and a fixing balloon for occluding the blood vessel attached to the tip portion of the catheter is expanded so as to stop the blood flow, and liquid (flush liquid) having little loss in the range of the wave length of the laser light in use is charged and replaced with blood so that the condition in the blood vessel is displayed on the screen under the condition that the vision is made transparent. Subsequently, after the diagnosis of the diseased part is performed, the fibers are replaced with a laser light applying fiber and in this condition, the laser light is applied to remove the diseased part.

In such a method, however, since it is impossible to observe the diseased part when projecting the laser light, it has been difficult to confirm whether or not the projection is accurately performed. Accordingly, it has been difficult to secure the quickness, safety and sureness of the treatment.

Therefore, there is designed an intravascular laser operating device having a catheter accommodating endoscopic optical fibers, illumination optical fibers and laser light projecting fibers.

However, in this device, since the laser light is an invisible light with a wave length of such as ultraviolet or infrared range, it is impossible to confirm an accurate laser light projection position and there has been a problem that it is difficult to project the laser light only onto the diseased part accurately. Moreover, there has been a further problem that it is difficult to accurately confirm with only an endoscopic observation about the position of a diseased part or whether or not the diseased part is completely removed using the laser light, and whether or not there have been removed a tissue more than required.

The present invention has been made considering the problems mentioned above and has as its object to provide an intravascular laser operating device capable of accurately discriminating a diseased part and confirming the laser projection position and of performing a sure treatment.

DISCLOSURE OF THE INVENTION

In order to accomplish the object mentioned above, the intravascular laser operating device of the present invention comprises a catheter accommodating endoscopic fibers for endoscopy of a diseased part in a vital blood vessel and laser light projecting fibers for applying laser light to the diseased part, a laser device for applying laser light to the laser light projecting fibers, an image forming device for obtaining the image representing the condition of the inside of a blood vessel based on the output light from the endoscopic fibers, and guide light applying means for applying guide light of a wave length which can be visualized by the image forming process by means of said image forming device and excited light for generating a fluorescent spectrum to said laser light projection fibers.

Herein, as the guide light applying means mentioned above, a wave length changing unit is used for changing a part of the laser light to a visible wave length through the image forming device.

According to the intravascular laser operating device constituted as described above, since the position projected by the laser light can be confirmed by observing the position having the guide light projected by means of the image forming device, the laser light can be surely projected only to the diseased part. Moreover, the diseased part can be discriminated by analyzing the fluorescent spectrum inside the blood vessel.

OPTIMUM EMBODIMENT OF THE INVENTION

An embodiment of the present invention is explained hereinafter with reference to the drawings.

Figure 1:
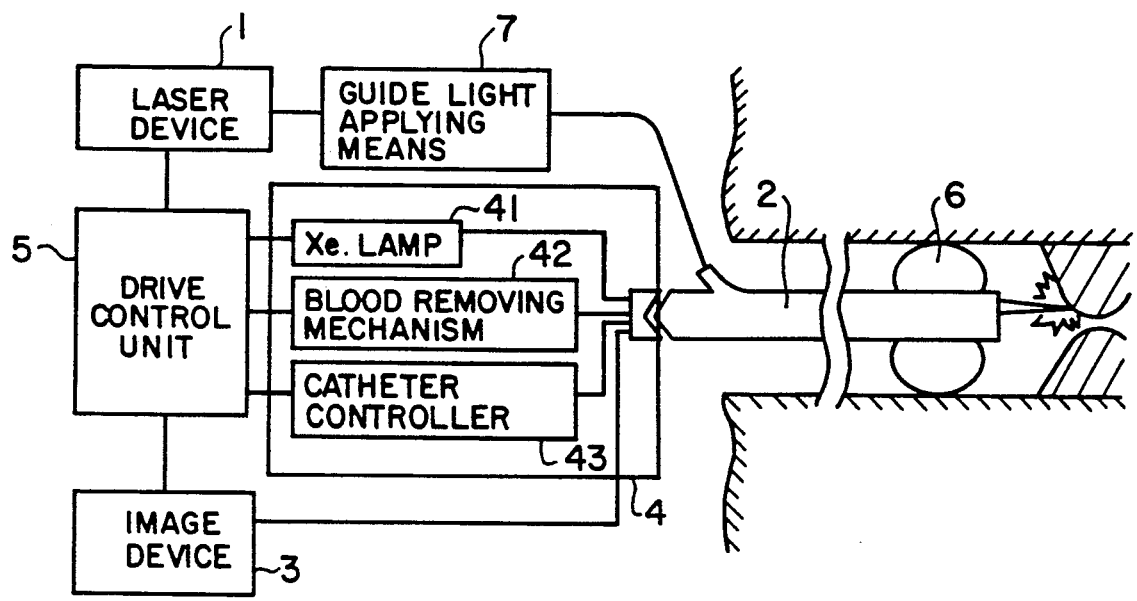
FIG. 1 is a schematic diagram showing an embodiment of an intravascular laser operating device.

As shown in FIG. 1, the intravascular laser operating device of the present embodiment comprises;

a laser device (1), an operating catheter (2) having endoscopic fibers for performing an endoscopy of a diseased part, a tip objective optical system, an illumination light guide, a flush liquid passage hole, a balloon dilation liquid passage hole, laser light illumination fibers and tip portion control wire, an image device (3) as an image forming device for forming an image representing the condition of the inside of the blood vessel based on the output light from the endoscopic fibers and for discriminating a diseased part by analyzing the fluorescent spectrum inside the blood vessel, a drive control unit (5) for applying light to said catheter (2) through an interface portion (4) and for supplying such as liquid, and guide light applying means (7) for applying the guide light an excited light for obtaining a fluorescent spectrum inside the blood vessel to said laser light projecting fibers. Moreover, (6) is a fixing balloon for occluding the blood vessel provided on the tip of the catheter (2). And said image device (3) has functions of such as displaying a form of the endoscopic image and displaying a fluorescent spectrum analysis and of recording an image.

Figure 2:
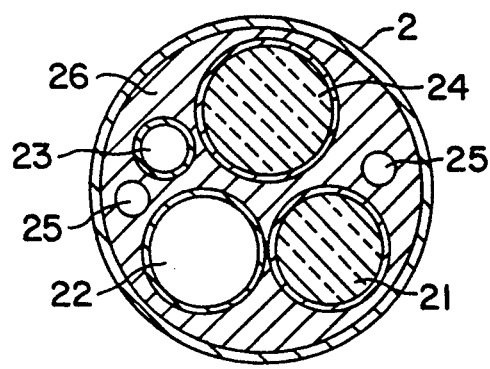
FIG. 2 is a sectional view of a catheter.

FIG. 2 is a sectional view of the catheter (2) which is made in the manner that, endoscopic fibers (21) and laser light projecting fibers (24) and a tip control wire (25) are bundled to be fixed in transparent medium (26), forming a flush liquid passage hole (22), a balloon dilation liquid passage hole (23), having the surface coated with a thin film. Moreover, said transparent medium (26) serves as the illumination light guide.

Moreover, it is not always necessary that said endoscopic fibers (21) and laser light projecting fibers (24) are fixed in the transparent medium (26), but there may be provided a proper through hole in the transparent medium (26), thereby removably inserting the fibers (21) and (24) therethrough.

The endoscopic fiber (21) is made of materials having little dispersion particularly in order to attain a high quality image, accomplishing the high accuracy of an edge optical systems. The laser light projecting fiber (24) is made of materials such as quartz with good transmittance through which near infrared rays can be transmitted with high density of energy, with low energy loss, and the end surface thereof is processed with high accuracy in order to suppress the heat generation at the end surface. The transparent medium (26) of which the illumination light guide is made, is composed of visible light transmittable materials with good flexibility such as multi-components group glass, plastic resin and rubber. The illumination light is projected from the tip section of the catheter (2). Using the tip control wire (25), which is controlled by a catheter controller (43), the tip of the catheter is guided to the diseased part by a catheter controller (43) to be mentioned later in order to face the tip of the catheter (2) to the diseased part.

The outer diameter of the catheter (2) accommodating the respective components (21) to (26) mentioned above has a thinned diameter of a few milli meters, preferably less than 1.5 mm. Therefore, it becomes possible to easily reach any part in the blood vessel by the guide of the catheter controller (43).

Figure 3:
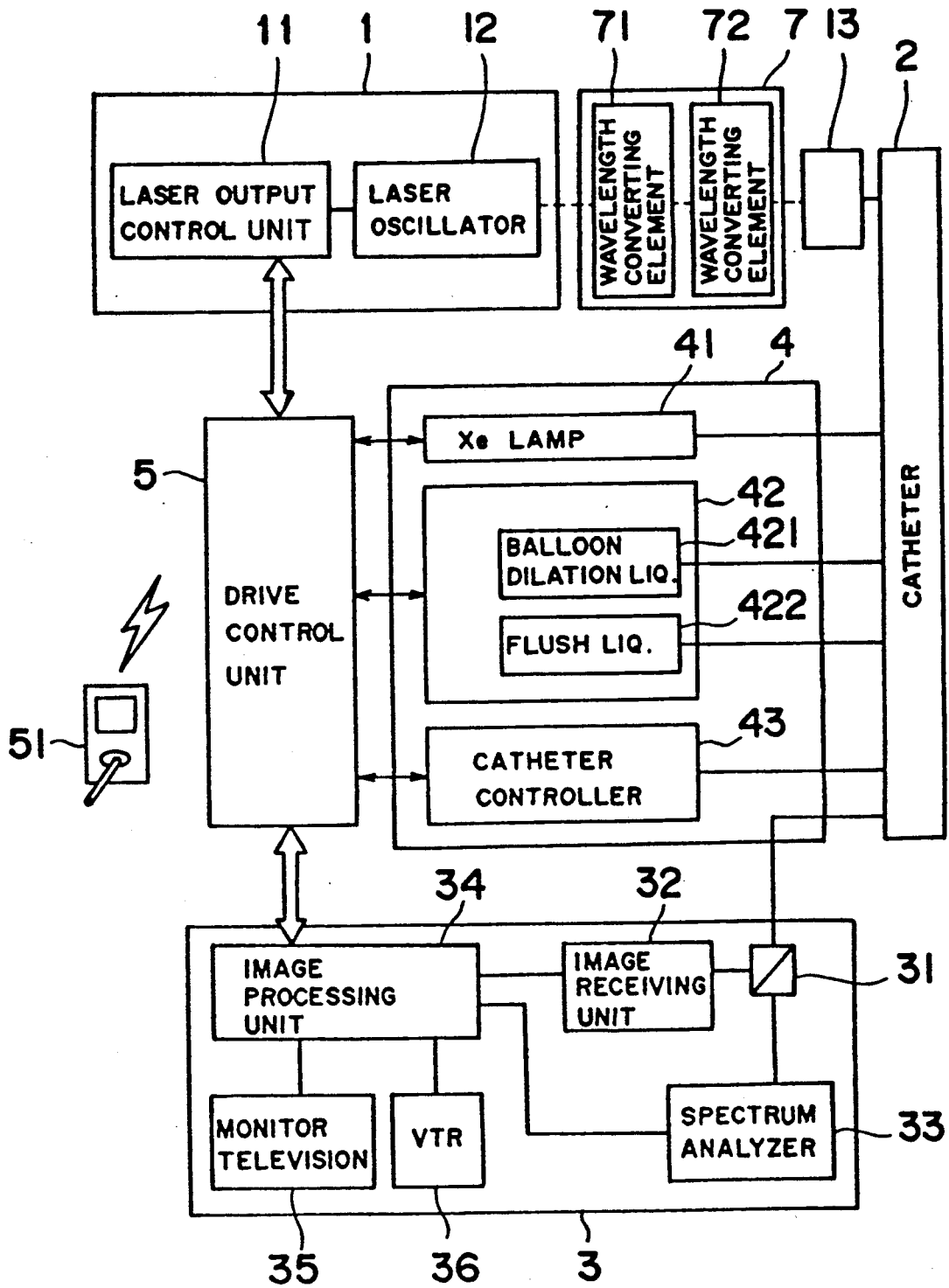
FIG. 3 is a block diagram showing such as a laser device, drive control unit and image device of the intravascular laser operating device.

FIG. 3 is a diagram showing the details of the laser device (1), guide light applying means (7), interface portion (4), drive controller (5) and image device (3).

The laser device (1) comprises a laser output controller (11) and laser oscillating unit (12), wherein the laser output controller (11) controls the power and pulse intervals of the laser light projected from the laser oscillating unit (12). The laser oscillating unit (12) is composed of a YAG laser using yttrium, aluminum and garnet ($Y_3Al_5O_{12}$) crystal including Nd (neodymium). Moreover, (13) denotes a connecting portion for connecting the projected laser light to the light leading fiber (24), which is composed of a minute optical system having little energy loss.

The guide light applying means (7) is composed of two wave length converting elements (71) (72) for converting the wave length of a part of the laser light. The wave length converting elements (71) (72), there are of optical fiber type or of thin film type forming optical wave leading paths by organic or inorganic second order non-linear optical materials. The near infrared laser light of 1.064 μm wave length projected from the YAG laser mentioned above is passed through the first wave length converting element (71) so as to be partially converted into a green light of 0.532 μm wave length. Subsequently said green light of 0.532 μm wave length and the near infrared laser light of 1.064 μm wave length are passed through the second wave length converting element (72); so as to be partially converted into a green light of 0.532 μm wave length and ultraviolet rays of 0.355 μm wave length and of 0.266 μm wave length. The lights of the respective wave lengths mentioned above are applied from the connecting portion (13) to the light leading fiber (24) so as to be transmitted through the light leading fiber (24) and projected from the tip of the catheter (2) to the diseased part. Moreover, the green light of 0.532 μm wave length is used as a guide light among the lights of the respective wave lengths generated by converting the wave length mentioned above, and the other ultraviolet rays are used for the fluorescent spectrum analysis to be described later.

The interface portion (4) comprises a Xe lamp (41) for applying a visible light to said illumination light guide (26), a blood removing mechanism (42) for charging balloon dilation liquid (421) (such as isotonic sodium chloride solution) and flush liquid (422) (liquid having little energy loss in the range of the wave length of the used laser) into the balloon dilation fluid passage hole (23) and flush liquid passage hole (22), and a catheter controller (43) having an operation mechanism for operating the control wire, which is controlled by the drive control unit (5). The drive control unit (5) controls said catheter controller (43) so as to reach the catheter (2) to a desired portion. The drive control unit (5) the ON/OFF and controls the Xe lamp (41) and the blood removing mechanism (42). Besides this, the drive control unit (5) sends a control signal to the laser output controller (11) so as to switch the ON/OFF and control the power of the laser output. In addition, the drive control unit (5) itself may be operated by a person monitoring the image device (3) or may be automatically operated by accommodating a microcomputer to produce a predetermined order signal based on a predetermined signal supplied from the image device (3). When a person performs, it may be controlled by a remote control unit (51); from an operating table for example.

The image device (3) comprises a division optical system (31) dividing an image light generated from the endoscopic fiber (21), image receiving unit (32) for receiving by CCD scanner one of the divided image lights, spectrum analyzing unit (33) obtaining the components of the fluorescent spectrum of the other divided image lights, image processing unit (34) compensating the output signals of the image receiving unit (32) and the spectrum analyzing unit (33), monitor television (35) displaying the processed image signal on the screen of the television, and VTR (36) for recording the image.

Figure 4:
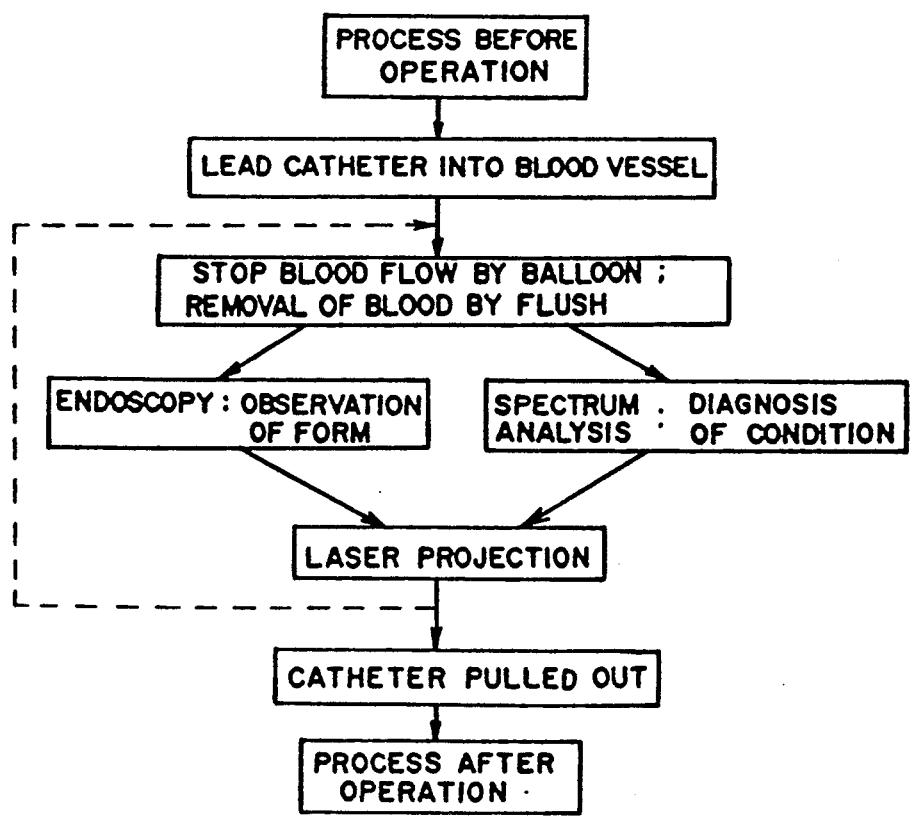
FIG. 4 is a flow chart showing an operating process of the intravascular laser operating device.

Next, the operating process of said intravascular laser operating device is explained with reference to Fig. 4. First, after the processes before operation such as a disinfection of the catheter inserting portion, anesthetization and drug supply are performed, the catheter controller (43) is driven through the drive control unit (5) so that the catheter (2) is guided into a predetermined blood vessel (such as a coronary artery). Subsequently, the balloon dilation liquid (421) is charged into the balloon dilation fluid passage hole (23) so that the balloon (6) is expanded for stopping the blood flow and the distal tip of the catheter (2) is fixed in the blood vessel by the balloon (6). The flush liquid (422) is quickly charged into the flush liquid passage hole (22) so that the blood in the lower stream below the blood flow stopped portion is replaced to be made transparent. By observing the monitor television (35), the projection laser light with its output lowered is projected to the tissue and the fluorescent spectrum generated by the ultraviolet rays of 0.355 $\mu$m and 0.266 $\mu$m wave lengths mentioned above included in the laser light is observed. Then the spectrum analyzer unit (33) diagnoses the diseased part, and if there is no diseased part, the balloon (6) is constricted to recover the flow of the blood and the catheter (2) is advanced to another portion. If there is a diseased part, the laser light is projected so as to destroy the diseased part. At this time, since the laser light projecting position can be confirmed by watching the projection position of the guide light by the monitor television (35), the laser light can be surely projected to the diseased part so that the treatment can be performed with good accuracy. Moreover, since the laser light can be projected watching the monitor television (35) or spectrum-diagnosing, it can be immediately judged whether or not the diseased part is completely destroyed. If not completely destroyed, the laser light is projected once more. Then, if there seems to be a time lapse, the balloon (6) is once constricted to release the occlusion (the release of occlusion is performed because it is undesirable to keep the occlusion for a long time), and subsequently the blood flow is stopped once more and the blood is replaced with the flush liquid (422) and the laser light is projected. The processes as mentioned above are repeated until the diseased part is completely destroyed. If the diseased part is completely destroyed, the balloon (6) is constricted and the occlusion is released and then the catheter (2) is pulled out. Finally, a necessary process after operation is performed and the operation is finished. Moreover, the processed result in the image device (3) may be judged by a microcomputer and all of the operations including the laser projection can be automatically and mechanically performed.

In addition, the image device (3) mentioned above may not comprise the spectrum analyzing unit (33) and in this case, since the ultraviolet rays of 0.355 $\mu$m or 0.266 $\mu$m wave length are not necessary, it is enough for the guide light applying means (7) to have only one wave length converting element. Moreover, said guide light is not limited to a visible light, there can be selected a light in the range of a wave length which is imagable by the image device (3). Furthermore, the image forming device is not limited to the image device (3) for electrically processing the output light from the endoscopic fibers as described above, and there may be used a device for forming an image depending on the output light of the optical system.

The above mentioned guide light applying means (7) is not limited to the wave length converting elements (71) and (72) and as shown in FIG. 5, for example, it may be a light source provided apart from the laser device (1) for treatment. The guide light applying means (7) shown in the figure is a laser device composed of a laser output control unit (73) and a laser oscillating unit (74), wherein the laser generates unit (74) oscillates a laser light of a wave length which can be visualized by processing the image. And the guide laser light generated from said guide light laser device (7) is combined with the laser light for treatment by combination optical systems (75) and (76) and is applied into the light leading fibers through the combination portion (13).

As described above, according to the intravascular laser operating device of the present invention, since the diseased part can be accurately discriminated and the position having the laser light projected can be confirmed depending on the position of the guide light, the laser light can be accurately projected to the diseased part. Accordingly, the diseased part can be quickly performed with safety and sureness. Moreover, because the wave length converting elements are used as the guide light applying means, since there is no need to provide a light source besides the laser device, the optical system can be simplified.

What is claimed is:

1. An intravascular laser operating device for examining and removing a diseased part in a blood vessel comprising:

a catheter having endoscopic fibers for performing an endoscopy and diagnosis of a diseased part in a blood vessel and laser light projecting fibers for projecting a laser light, a visible guide light, and an excitation light to the diseased part;

a laser device for generating laser light;

guide light applying means for applying said laser light, visible guide light, and excitation light to said laser light projecting fibers; said guide light to said laser light projecting fibers; said guide light applying means comprising first and second wave length converting element means; said first wave length converting element means for converting a wavelength of part of the laser light from said laser device into the visible guide light; said second wave length converting element means for converting a wavelength of part of the visible guide light into the excitation light; said excitation light for generating a fluorescent spectrum;

an image forming device for obtaining an image representing the condition of the inside of the blood vessel based on image light received by the endoscopic fibers; said image forming device comprising:

an optical system for dividing the image light received by the endoscopic fibers into at least a first and second portion, an image receiving means for receiving said first portion of said image light, and spectrum analyzing means for diagnosing the diseased part by obtaining a fluorescent spectrum of said second portion of said image light.

2. The intravascular laser operating device of claim 1, wherein the first and second wave length converting element means are made of second order non-linear optical materials.

3. The intravascular laser operating device of claim 2, wherein said laser device comprises a laser oscillating means for generating the laser light and laser output control means for controlling the power and pulse intervals of the laser light generated from said laser oscillating means, and said laser oscillating means comprises a YAG laser.

4. The intravascular laser operating device of claim 1, wherein the excited light for generating the fluorescent spectrum is composed of ultraviolet rays.

5. A method of performing laser surgery on a diseased part in a blood vessel comprising:
 (a) inserting a catheter into a blood vessel, the catheter having endoscopic fibers for performing an endoscopy and diagnosis of a diseased part in a blood vessel and laser light projecting fibers for projecting a laser light, a visible guide light, and an excitation light to the diseased part;
 (b) generating laser light with a laser device at a low output power level;
 (c) converting a wavelength of part of the laser light from the laser device into the visible guide light;
 (d) converting a wavelength of part of the visible guide light into the excitation light; said excitation light for generating a fluorescent spectrum;
 (e) applying said laser light, said visible guide light, and said excitation light to said laser light projecting fibers;
 (f) obtaining a diagnostic image representing the condition of the inside of the blood vessel based on an endoscopic image received by the endoscopic fibers;
 (g) diagnosing the diseased part by obtaining a fluorescent spectrum of the diagnostic image;
 (h) if no diseased part is found, advancing the catheter to another portion of the blood vessel and repeating steps (a) through (g); otherwise
 (i) increasing the output power of the applied laser light to destroy the diseased part;
 (j) repeating steps (g) through (i) until the diseased part is completely destroyed.

* * * * *